(12) United States Patent
Ries et al.

(10) Patent No.: US 7,534,271 B2
(45) Date of Patent: May 19, 2009

(54) FEMORAL HIP PROSTHESIS AND METHOD OF IMPLANTATION

(75) Inventors: Michael Ries, Tiburon, CA (US); T. Wade Fallin, Hyde Park, UT (US); Daniel F. Justin, Logan, UT (US); Mark A. Munt, Moab, UT (US)

(73) Assignee: Smith + Nephew, Memphis, TN (US)

( * ) Notice: Subject to any disclaimer, the term of this patent is extended or adjusted under 35 U.S.C. 154(b) by 562 days.

(21) Appl. No.: 10/763,314

(22) Filed: Jan. 22, 2004

(65) Prior Publication Data

US 2005/0165493 A1    Jul. 28, 2005

(51) Int. Cl.
*A61F 2/36* (2006.01)
(52) U.S. Cl. .................... 623/23.21; 623/23.35
(58) Field of Classification Search .............. 623/23.21, 623/23.22, 23.24, 23.25, 23.26, 23.35
See application file for complete search history.

(56) References Cited

U.S. PATENT DOCUMENTS

| | | | |
|---|---|---|---|
| 3,512,184 A | 5/1970 | Grove | |
| 3,658,056 A | 4/1972 | Huggler et al. | |
| 3,683,421 A | 8/1972 | Martinie | |
| 3,782,373 A | 1/1974 | Smythe | |
| 3,848,272 A | 11/1974 | Noiles | |
| 3,864,758 A | 2/1975 | Yakich | |
| 3,871,031 A | 3/1975 | Boutin | |
| 3,894,297 A | 7/1975 | Mittelmeier et al. | |
| 3,916,451 A | 11/1975 | Buechel et al. | |
| 4,001,897 A | 1/1977 | Rambert et al. | |
| 4,005,495 A | 2/1977 | Locke et al. | |
| 4,012,795 A | 3/1977 | Dorre et al. | |
| 4,012,796 A | 3/1977 | Weisman et al. | |
| 4,021,865 A | 5/1977 | Charnley | |
| 4,080,666 A | 3/1978 | Fixel | |
| 4,129,903 A | 12/1978 | Huggler | |
| 4,187,559 A | 2/1980 | Grell et al. | |
| 4,224,699 A | 9/1980 | Weber | |
| 4,274,164 A | 6/1981 | Rehder et al. | |
| 4,312,079 A | 1/1982 | Dorre et al. | |
| 4,314,381 A | 2/1982 | Koeneman | |
| 4,332,036 A | 6/1982 | Sutter et al. | |
| 4,454,612 A | 6/1984 | McDaniel et al. | |
| 4,488,320 A | 12/1984 | Wilson | |

(Continued)

FOREIGN PATENT DOCUMENTS

EP    159510  A2    3/1985

(Continued)

*Primary Examiner*—Bruce E Snow
(74) *Attorney, Agent, or Firm*—David W. Meibos; Daniel F. Justin; Barbara Daniels

(57) ABSTRACT

Implants and methods are presented for surgically repairing a hip joint with a proximal femoral prosthesis that comprises femoral head component and a femoral stem component. The femoral stem component comprising a neck portion, a flange portion, a transitional body region and an elongated stem. The femur is prepared for implantation of the femoral hip prosthesis by resecting the proximal femur and reaming a symmetric intramedullary cavity in the femur. The femoral hip prosthesis is then inserted the on the resected femur and in the intramedullary cavity. The femoral hip prosthesis elastically deforms when loaded during use to apply dynamic compressive loads and displacement to the calcar region of the resected proximal femur.

20 Claims, 8 Drawing Sheets

U.S. PATENT DOCUMENTS

| | | |
|---|---|---|
| 4,530,114 A | 7/1985 | Tepic |
| 4,532,661 A | 8/1985 | Halpern |
| 4,546,501 A | 10/1985 | Gustilo et al. |
| 4,549,319 A | 10/1985 | Meyer |
| 4,608,052 A | 8/1986 | Van Kampen et al. |
| 4,608,055 A | 8/1986 | Morrey et al. |
| 4,619,659 A | 10/1986 | Witzel |
| 4,623,349 A | 11/1986 | Lord |
| 4,645,506 A | 2/1987 | Link |
| 4,661,112 A | 4/1987 | Muller |
| 4,664,668 A | 5/1987 | Beck et al. |
| 4,670,015 A | 6/1987 | Freeman |
| 4,676,799 A | 6/1987 | Legrand |
| 4,681,590 A | 7/1987 | Tansey |
| 4,686,971 A | 8/1987 | Harris et al. |
| RE32,488 E | 9/1987 | Gustilo et al. |
| 4,693,724 A | 9/1987 | Rhenter et al. |
| 4,718,912 A | 1/1988 | Crowninshield |
| 4,718,916 A | 1/1988 | Morscher |
| 4,728,334 A | 3/1988 | Spotorno |
| 4,728,335 A | 3/1988 | Jurgutis |
| 4,731,088 A | 3/1988 | Collier |
| 4,750,905 A | 6/1988 | Koeneman et al. |
| 4,752,296 A | 6/1988 | Buechel et al. |
| 4,770,660 A | 9/1988 | Averill |
| 4,770,661 A | 9/1988 | Oh |
| 4,775,381 A | 10/1988 | Tari et al. |
| 4,778,469 A | 10/1988 | Lin et al. |
| 4,790,852 A | 12/1988 | Noiles |
| 4,792,337 A | 12/1988 | Muller |
| 4,795,472 A | 1/1989 | Crowninshield et al. |
| 4,795,473 A | 1/1989 | Grimes |
| 4,822,368 A | 4/1989 | Collier |
| 4,840,632 A | 6/1989 | Kampner |
| 4,846,839 A | 7/1989 | Noiles |
| 4,846,840 A | 7/1989 | Leclercq et al. |
| 4,846,841 A | 7/1989 | Oh |
| 4,851,004 A | 7/1989 | Homsy |
| 4,851,007 A | 7/1989 | Gray |
| 4,851,008 A | 7/1989 | Johnson |
| 4,871,369 A | 10/1989 | Muller |
| 4,878,917 A | 11/1989 | Kranz et al. |
| 4,881,536 A | 11/1989 | Noble et al. |
| 4,888,023 A | 12/1989 | Averill et al. |
| 4,888,024 A | 12/1989 | Powlan |
| 4,892,551 A | 1/1990 | Haber |
| 4,904,266 A | 2/1990 | Barber |
| 4,904,268 A | 2/1990 | Alvarado |
| 4,908,034 A | 3/1990 | Weightman et al. |
| 4,908,036 A | 3/1990 | Link et al. |
| 4,911,722 A | 3/1990 | Crespy |
| 4,936,863 A | 6/1990 | Hofmann |
| 4,938,771 A | 7/1990 | Vecsei et al. |
| 4,938,773 A | 7/1990 | Strand |
| 4,944,761 A | 7/1990 | Stuhmer et al. |
| 4,944,762 A | 7/1990 | Link et al. |
| 4,976,740 A | 12/1990 | Kleiner |
| 4,986,834 A | 1/1991 | Smith et al. |
| 4,995,883 A | 2/1991 | Demane et al. |
| 4,998,937 A | 3/1991 | Grimes |
| 5,002,578 A | 3/1991 | Luman |
| 5,002,579 A | 3/1991 | Copf et al. |
| 5,002,580 A | 3/1991 | Noble et al. |
| 5,002,581 A | 3/1991 | Paxson et al. |
| 5,004,476 A | 4/1991 | Cook |
| 5,007,935 A | 4/1991 | Vincent et al. |
| 5,030,234 A | 7/1991 | Pappas et al. |
| 5,035,712 A | 7/1991 | Hoffman |
| 5,035,717 A | 7/1991 | Brooks |
| 5,047,060 A | 9/1991 | Henssge et al. |
| 5,047,062 A | 9/1991 | Pappas et al. |
| 5,057,101 A | 10/1991 | Dorr et al. |
| 5,080,685 A | 1/1992 | Bolesky et al. |
| 5,087,260 A | 2/1992 | Fixel |
| 5,108,451 A | 4/1992 | Forte |
| 5,108,452 A | 4/1992 | DeMane et al. |
| 5,116,377 A | 5/1992 | Skripitz et al. |
| 5,116,380 A | 5/1992 | Hewka et al. |
| 5,133,764 A | 7/1992 | Pappas et al. |
| 5,133,766 A | 7/1992 | Halpern |
| 5,152,795 A | 10/1992 | Sioshansi et al. |
| 5,156,624 A | 10/1992 | Barnes |
| 5,163,963 A | 11/1992 | Hewka et al. |
| 5,163,964 A | 11/1992 | Lazzeri et al. |
| 5,181,928 A | 1/1993 | Bolesky et al. |
| 5,197,988 A | 3/1993 | Spotorno et al. |
| 5,197,989 A | 3/1993 | Hinckfuss et al. |
| 5,197,990 A | 3/1993 | Lawes et al. |
| 5,201,771 A | 4/1993 | Belykh et al. |
| 5,201,882 A | 4/1993 | Paxson |
| 5,222,985 A | 6/1993 | Homsy |
| 5,246,461 A | 9/1993 | Tepic |
| 5,258,033 A | 11/1993 | Lawes et al. |
| 5,286,260 A | 2/1994 | Bolesky et al. |
| 5,314,489 A | 5/1994 | Hoffman et al. |
| 5,336,265 A | 8/1994 | Serbousek et al. |
| 5,370,706 A | 12/1994 | Bolesky et al. |
| 5,376,124 A | 12/1994 | Gustke et al. |
| 5,376,125 A | 12/1994 | Winkler |
| 5,376,126 A | 12/1994 | Lin |
| 5,387,244 A | 2/1995 | Breard |
| 5,389,107 A | 2/1995 | Nassar et al. |
| 5,458,653 A | 10/1995 | Davidson |
| 5,458,654 A | 10/1995 | Tepic |
| 5,468,243 A | 11/1995 | Halpern |
| 5,480,452 A | 1/1996 | Hofmann |
| 5,480,453 A | 1/1996 | Burke |
| 5,507,814 A | 4/1996 | Gilbert et al. |
| 5,507,830 A | 4/1996 | DeMane et al. |
| 5,514,182 A | 5/1996 | Shea |
| 5,514,184 A | 5/1996 | Doi et al. |
| 5,549,704 A | 8/1996 | Sutter |
| 5,571,195 A | 11/1996 | Johnson |
| 5,571,203 A | 11/1996 | Masini |
| 5,591,233 A | 1/1997 | Kelman et al. |
| 5,653,764 A | 8/1997 | Murphy |
| 5,653,765 A | 8/1997 | McTighe et al. |
| 5,702,448 A | 12/1997 | Buechel et al. |
| 5,702,483 A | 12/1997 | Kwong |
| 5,702,487 A | 12/1997 | Averill et al. |
| 5,725,590 A | 3/1998 | Maumy et al. |
| 5,725,592 A | 3/1998 | White et al. |
| 5,725,593 A | 3/1998 | Caracciolo |
| 5,725,594 A | 3/1998 | McTighe et al. |
| 5,725,595 A | 3/1998 | Gustilo |
| 5,746,771 A | 5/1998 | Clement, Jr. et al. |
| 5,755,807 A | 5/1998 | Anstaett et al. |
| 5,800,553 A | 9/1998 | Albrektsson et al. |
| 5,800,560 A | 9/1998 | Draenert |
| 5,814,050 A | 9/1998 | Benson |
| 5,858,020 A | 1/1999 | Johnson et al. |
| 5,861,042 A | 1/1999 | Buechel et al. |
| 5,876,459 A | 3/1999 | Powell |
| 5,888,208 A | 3/1999 | Ro |
| 5,906,644 A | 5/1999 | Powell |
| 5,954,771 A | 9/1999 | Richelsoph et al. |
| 5,980,575 A | 11/1999 | Albrektsson et al. |
| 6,010,535 A | 1/2000 | Shah |
| 6,120,544 A | 9/2000 | Grundei et al. |
| 6,179,877 B1 * | 1/2001 | Burke ..................... 623/22.12 |
| 6,193,761 B1 | 2/2001 | Treacy |
| 6,197,065 B1 | 3/2001 | Martin et al. |
| 6,231,611 B1 | 5/2001 | Mosseri |
| 6,273,915 B1 | 8/2001 | Grimes |

| | | |
|---|---|---|
| 6,284,002 B1 | 9/2001 | Sotereanos |
| 6,290,726 B1 | 9/2001 | Pope et al. |
| 6,379,390 B1 | 4/2002 | Advani et al. |
| 6,383,226 B1 | 5/2002 | Carter et al. |
| 6,383,227 B1 | 5/2002 | Baroud et al. |
| 6,395,004 B1 | 5/2002 | Dye et al. |
| 6,402,753 B1 | 6/2002 | Cole et al. |
| 6,402,787 B1 | 6/2002 | Pope et al. |
| 6,413,280 B1 | 7/2002 | Feiler |
| 6,428,578 B2 | 8/2002 | White |
| 6,432,141 B1 | 8/2002 | Stocks et al. |
| 6,482,237 B2 | 11/2002 | Mosseri |
| 6,488,714 B2 | 12/2002 | Keller |
| 6,488,716 B1 | 12/2002 | Huang |
| 6,503,281 B1 | 1/2003 | Mallory |
| 6,514,288 B2 | 2/2003 | Meulink et al. |
| 6,524,343 B2 | 2/2003 | Storer et al. |
| 2002/0072805 A1 | 6/2002 | Sullivan et al. |
| 2002/0107520 A1 | 8/2002 | Hoffman |
| 2002/0111692 A1 | 8/2002 | Ralph et al. |
| 2002/0133234 A1 | 9/2002 | Sotereanos |
| 2002/0143402 A1 | 10/2002 | Steinberg |
| 2002/0156536 A1 | 10/2002 | Harris et al. |
| 2003/0014123 A1 | 1/2003 | Copf et al. |
| 2003/0033020 A1 | 2/2003 | Hunter et al. |
| 2003/0045941 A1 | 3/2003 | Lewallen |
| 2003/0050704 A1 | 3/2003 | Keynan |
| 2003/0060891 A1 | 3/2003 | Shah |
| 2003/0065397 A1 | 4/2003 | Hanssen et al. |
| 2003/0074079 A1 | 4/2003 | McTighe et al. |
| 2003/0074080 A1 | 4/2003 | Murray |
| 2003/0074083 A1 | 4/2003 | LeGros et al. |
| 2003/0088316 A1 | 5/2003 | Ganjianpour |
| 2003/0109933 A1 | 6/2003 | Weissman et al. |
| 2003/0120347 A1 | 6/2003 | Steinberg |
| 2003/0130740 A1 | 7/2003 | Stocks et al. |
| 2003/0171819 A1 | 9/2003 | Sotereanos |

FOREIGN PATENT DOCUMENTS

| | | |
|---|---|---|
| EP | 145617 A2 | 6/1985 |
| EP | 128036 B1 | 5/1987 |
| EP | 220803 A2 | 5/1987 |
| EP | 065481 B1 | 8/1987 |
| EP | 266081 A1 | 5/1988 |
| EP | 145617 B1 | 6/1988 |
| EP | 310566 A2 | 4/1989 |
| EP | 159510 B1 | 5/1990 |
| EP | 539036 A1 | 4/1993 |
| EP | 539036 B1 | 11/1996 |
| EP | 761183 B1 | 5/2002 |
| EP | 728449 B1 | 7/2002 |
| EP | 1234556 A2 | 8/2002 |
| EP | 841041 B1 | 9/2002 |
| EP | 1240879 A2 | 9/2002 |
| EP | 966240 B1 | 10/2002 |
| EP | 852931 B1 | 2/2003 |
| WO | WO8700033 A1 | 1/1987 |
| WO | WO9600539 A1 | 1/1996 |
| WO | WO9806359 A1 | 2/1998 |
| WO | WO0048535 A1 | 8/2000 |
| WO | WO03007852 A1 | 1/2003 |
| WO | WO03094803 A1 | 11/2003 |

* cited by examiner

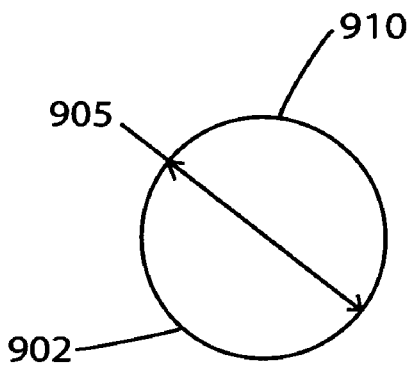
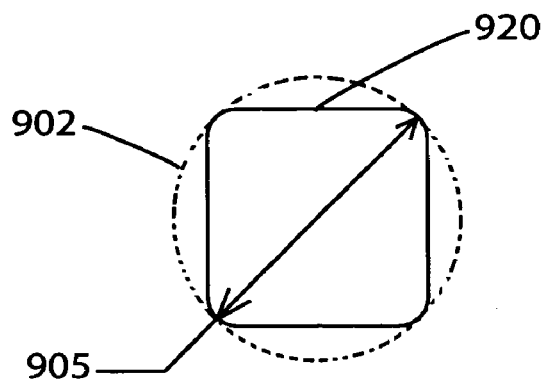
Fig. 4a    Fig. 4b
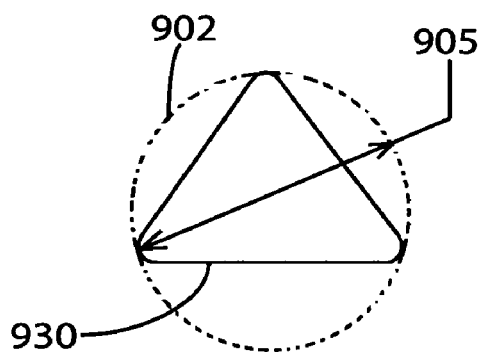
Fig. 4c
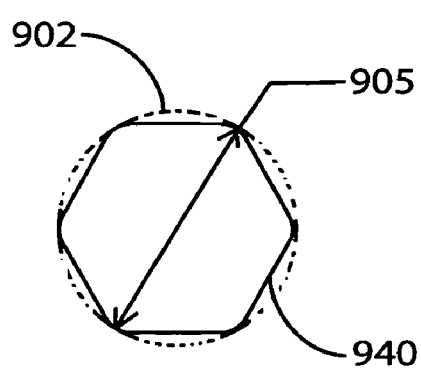
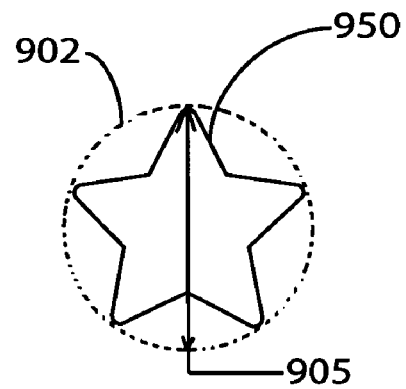
Fig. 4d    Fig. 4e

FEMORAL HIP PROSTHESIS AND METHOD OF IMPLANTATION

CROSS-REFERENCE TO RELATED APPLICATIONS

Not applicable.

BACKGROUND OF THE INVENTION

1. The Field of the Invention

The present invention relates to a femoral hip prosthesis for replacing a portion of proximal femoral bone during hip replacement and the methods of assembly and use thereof.

2. The Relevant Technology

Total hip arthroplasty using a metallic hip prosthesis has been successfully performed since the early 1960's and is now a routine procedure to address orthopedic diseases such as osteoarthritis, fracture, dislocations, rheumatic arthritis, and aseptic or avascular bone necrosis. During this procedure, the bone is prepared for the prosthesis by removing the damaged articulating end of the bone by resecting a portion of the bone including the femoral head. This exposes the inside, of the metaphaseal region of the intramedullary canal in the proximal femur. The surgeon then drills or reams a cavity in the femur approximately in line with the intramedullary canal. This cavity is used to align other tools such as reamers, broaches and other bone tissue removal instruments to create a roughly funnel shaped bone cavity that is smaller in cross-section as it extends down from the bone resection at the proximal end of the femur into the distal intramedullary canal. This funnel shaped cavity is typically also eccentric with more bone material removed from the medial calcar region of the proximal femur than the region on the lateral side of the canal.

Oftentimes a grouting agent commonly referred to as bone cement is then added to the funnel shaped cavity. Once the prosthesis is inserted into the cavity, this creates a bone cement mantle between the prosthesis and the bone. Sometimes the shape of the cavity is prepared to closely match the shape of the external surface of the prosthesis, and the prosthesis is press fit into the cavity without the use of bone cement. These press-fit prostheses typically have a textured bone-ingrowth surfaces place strategically at specific locations on their surface to help facilitate lone-term bone tissue growth into the prosthesis. This bone ingrowth into the porous structure on the implant creates a long lasting secure bond between the prosthesis and the proximal femur.

Once the bone cavity is prepared, the prosthesis is placed into the bone cavity and is supported directly by internal bone tissue in the case of a press fit implant or indirectly by the bone cement mantle in the case of the cemented implant. Then, the prosthesis is aligned such that the articulating end of the implant articulates with the opposite side of the natural joint in the case of a hemiarthoplasty, or articulates with a corresponding implant replacing the opposite side of the joint in the case of a total joint arthroplasty.

Current designs of proximal femur hip prosthesis have eccentric, non-symmetric cone shaped central body portions. The current methods of implant fixation allow for transfer of axial loads to the proximal femur mainly through shear stresses at the eccentric funnel shaped bone-prosthesis interface. The effective transfer of load is significantly dependent on the three-dimensional shape of funnel shaped cavity, the bone-prosthesis or bone-cement-prosthesis interface as well as physiological loading of the proximal end. Partly because of the eccentrically shaped cross-section of the central body portion, these currently available prostheses transmit radial expansion forces on the proximal femoral cavity as the implant is loaded in compression. The funnel shape of the cavity and the matching shape of the implant or bone cement result in circumferential hoop stresses and radial expansion stresses are distributed to the bone as the femoral component is axially loaded. This results in complex axial and shear stresses at the bone-implant interface. Consequently, the distribution of the loads that transmit from the femoral head axially through the proximal femur is altered after THA.

A potential cause of failure of currently used prosthesis is associated with the possible resorption of the bone surrounding the implant. The bone resorption can be the result of an altered distribution of shear stresses on the remaining proximal femoral tissue. In time, the lack of adequate stress transfer from the metal stem to the surrounding bone may cause a loss of bone density, resulting in the increased possibility of bone failure or loosening of the bone-prosthesis interface. The gradual loss of bone support in the calcar region of the eccentric cavity increases the bending load that must be borne by the prosthesis. This increase in bending load on the prosthesis can lead to stress shielding by the prosthesis resulting in prosthesis fatigue and potentially to eventual clinical failure.

SUMMARY

The present invention is directed to a femoral hip prosthesis that satisfies the need for anatomically distributing the dynamic compressive loads on the hip joint to the proximal femoral bone. The femoral hip prosthesis is adapted for implantation against a resected surface on a proximal end of a femur, and also in an intramedullary cavity of the femur. The femoral hip prosthesis comprises femoral head component and a femoral stem component. The femoral stem component comprises a neck portion, a flange portion, a transitional body portion, and an elongated stem portion. The neck portion comprises a proximal male friction fit portion and a distal neck body. The flange portion is distal and adjacent to the neck portion and is attached to the distal neck body. The flange portion comprises an upper portion and a bottom surface. The transitional body region is adjacent to the bottom surface of the flange portion and also extends from the distal neck body. The elongated stem portion extends distally from the transitional body region and is aligned with a longitudinal axis. The longitudinal axis is oriented at an acute angle relative to the bottom surface of the flange portion. The elongated stem portion comprises a uniform envelope that may contain rotation-restricting splines, a tapered portion or a transverse slot. The femoral hip prosthesis may also alternatively contain a rotation-restricting boss that is attached to the bottom of the flange portion. The femoral hip prosthesis also comprises a distal end tip portion on the distal end of the elongated stem portion.

DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 4a is an embodiment of a substantially circular cross-section of the elongated stem portion;

FIG. 4b is an embodiment of a substantially square cross-section of the elongated stem portion;

FIG. 4c is an embodiment of a substantially triangular cross-section of the elongated stem portion;

FIG. 4d is an embodiment of a substantially hexagonal cross-section of the elongated stem portion;

FIG. 4e is an embodiment of a substantially star shaped cross-section of the elongated stem portion;

DETAILED DESCRIPTION OF THE PREFERRED EMBODIMENTS

Figure 1:
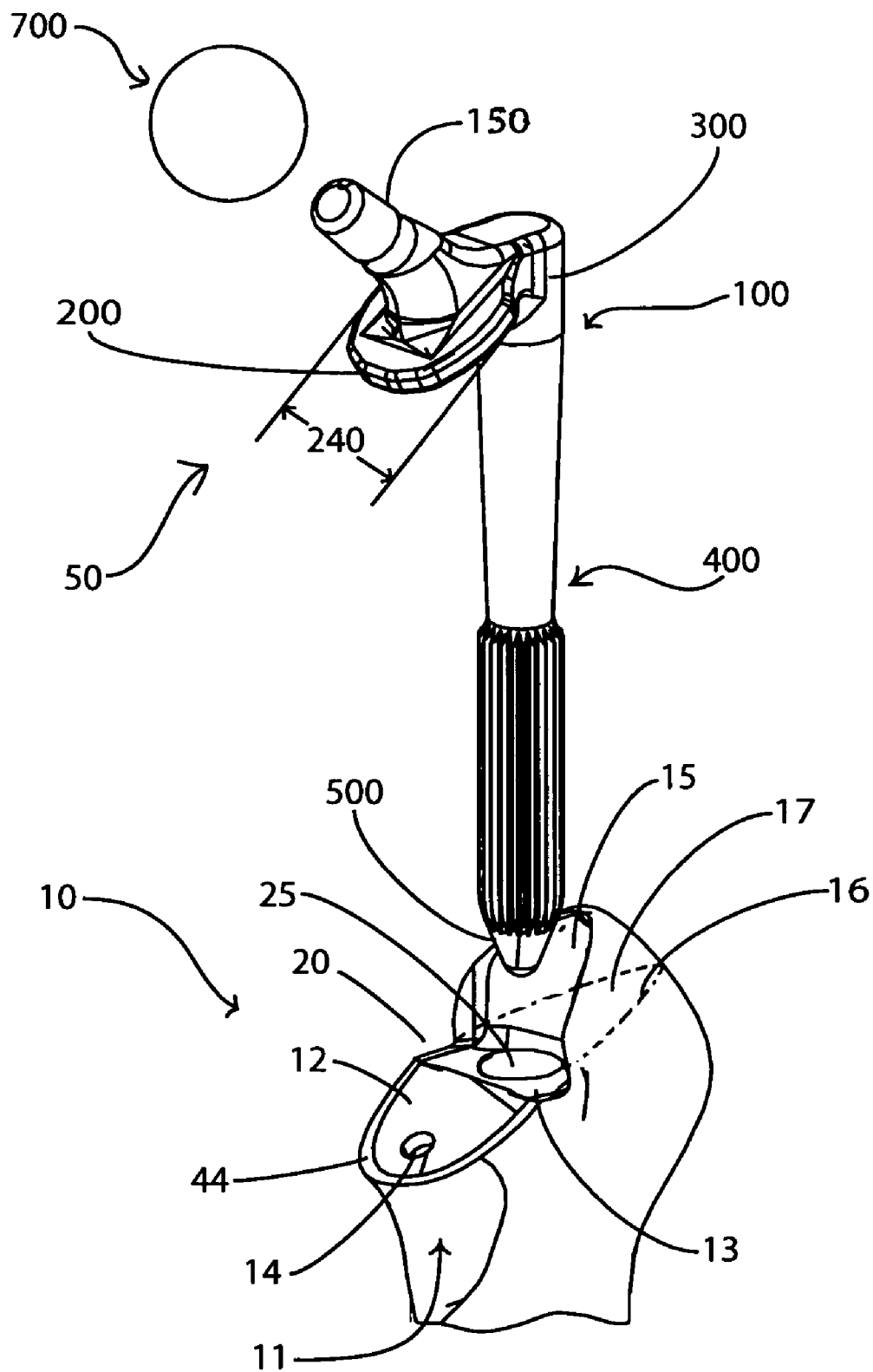
FIG. 1 is a perspective view of the show from the anteriomedial direction showing the femoral hip prosthesis including the before it is inserted into the resected proximal femur.

Depicted in FIGS. 1 through 7 are different embodiments of an implantable proximal femoral hip prosthesis 50 and methods of implantation therein. These embodiments of a hip joint replacement procedure and the design of the femoral hip prosthesis 50 that is meant to restore the biomechanical function of the hip joint while maintaining a secure interface with the proximal femur 10 and help to preserve anatomical loading of the remaining bone that surrounds the femoral hip prosthesis 50 once it is implanted. This allows the loads on the hip joint to be distributed optimally to the proximal femur 10.

The femoral hip prosthesis 50 comprises a femoral head component 700 and a femoral stem component 100. The femoral stem component 100 comprises a neck portion 150, a flange portion 200, a transitional body portion 300, an elongated stem portion 400, and a distal tip end 500. The non-eccentric symmetrical shape of the interface between the elongated stem portion 400 of the femoral stem component 100 and a cavity 25 along with the contact at the interface between a proximal resection 20 and the femoral stem component 100 helps to stabilize the femoral hip prosthesis 50 and transfer more anatomic loads from the prosthesis 50 to the bone efficiently.

Figure 2:
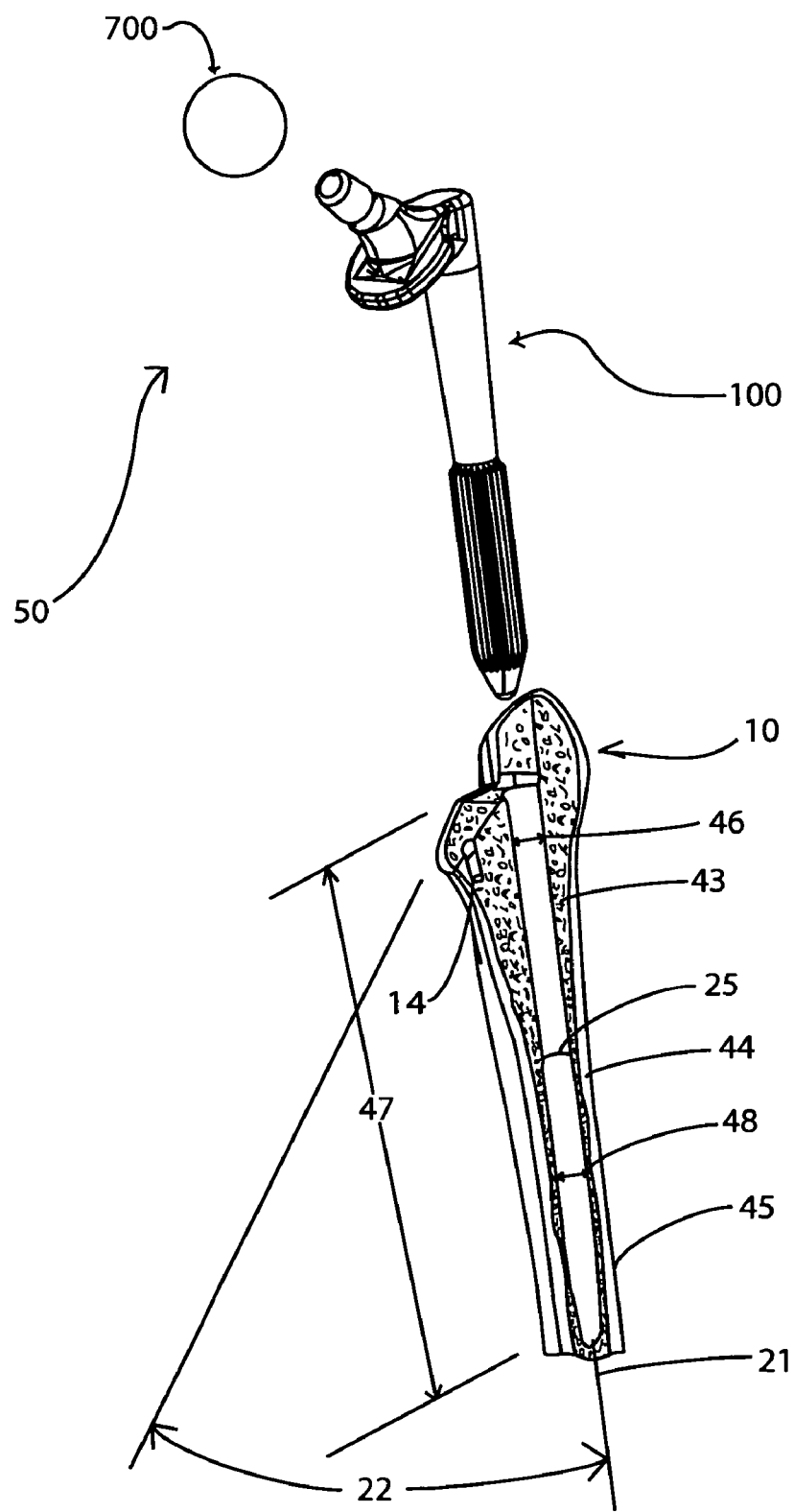
FIG. 2 is a perspective view shown form the anteriomedial direction showing the femoral hip prostheses before it is inserted and a cross-sectional view of the resected proximal femur with the intramedullary cavity and the boss cavity prepared.

To prepare the patient for a proximal femoral hip prosthesis 50, the surgeon first makes an incision or incisions near the hip joint, then the surgeon cuts though some of the tissue near the articulating joint, and retracts these tissues apart to visualize and access the diseased bone structures that are to be replaced by the hip joint replacement prostheses. FIG. 1, is a simplified perspective view from the anteriomedial direction showing the proximal femur 10 and the femoral hip prosthesis 50, showing the femoral head component 700, the femoral stem component 100, and the proximal femur 10. For clarification, all of the other tissues necessary to provide function to the hip joint are not shown in this simplified view. The surgeon aligns bone tissue removal tools, such as drills, reamers, or broaches (not shown) with alignment instrumentation (not shown) to form a substantially non-eccentric, symmetric intramedullary cavity 25 in the cancellous bone 3 of the proximal femur 10 that is in longitudinal alignment with the shaft 45 of the proximal femur 10. The intramedullary cavity 25 is formed with a cross-sectional shape, such as a diameter 46 as shown in an embodiment of the intramedullary cavity 25 shown in FIG. 2. The diameter 46 is the measurement of the diameter of the maximum circular periphery that encompasses an envelope that the cross-sectional shape of the intramedullary cavity 25 comprises. The shape of the intramedullary cavity 25 can also be substantially non-eccentric, symmetric, non-circular shapes such as a square (not shown), star shape, (not shown), hexagon (not shown), or other parallelogram shape. Matching non-circular shapes of both the femoral stem component 100 and the intramedullary cavity 25 are potentially more efficient at restricting torsional movement between the femoral stem component 100 and the proximal femur 10 than circular cross-sectional shapes. The intramedullary cavity 25 also is formed to a length 47 as also shown in FIG. 2. The cross-sectional shape, diameter 46 and length 47 of the intramedullary cavity 25 in the proximal femur 10 is dependent on the morphology, structure, and pathology of the patient anatomy and the anticipated biomechanical in vivo loads resulting from the use of the femoral stem component 100.

The intramedullary cavity 25 may have a multiple diameters, or in the case of non-circular cross-sectionally shaped cavities multiple sizes, to approximately match the shape of the femoral stem component 100. FIG. 2, which illustrates a cross-sectional view of the proximal femur 10, shows that both a first diameter 46 and a second diameter 48 can form an intramedullary cavity 25 is shown in FIG. 2. The second diameter 48 in the embodiment of FIG. 2 is smaller than the first diameter 46. Additionally, a third, forth, fifth, or more diameters (all not shown) can form the intramedullary cavity 25. For the purposes of clarity of illustration, the cross-section of the intramedullary cavity on FIG. 1 and FIG. 2 are circular, resulting in a substantially cylindrical opening. Correspondingly different size or shaped tissue removal tools (not shown) are used to prepare an intramedullary cavity 25 with more than one size diameter 46. The surgeon may also find it advantageous to form different or alternating shapes of cross-sections in the symmetric, non-eccentric intramedullary cavity 25. For example, the cavity may be first diameter circular, and then square, then a second diameter circle, then a star shape, then cone shaped, then finally spherically shaped at its deepest, most distal end.

After the basic intramedullary cavity 25 is formed, instrumentation (not shown) is used to align cutting guides for bone cutting instruments (not shown) to form a proximal resection 20 on the proximal femur 10. The proximal resection 20 may have different surfaces such as a calcar resection surface 12 that is formed when the femoral calcar 11 is transverely cut through the proximal femur 10. The calcar resection surface 12 is cut at an acute angle 22 with respect to the longitudinal axis 21 of the proximal femur 10. This acute angle is typically between 10° and 80°. Although the proximal resection 20 may be simply one continuous transverse cut that passes from the medial to the lateral side of the proximal femur in the direction and plane defined by a the plane outlined by the dashed line 16 shown in FIG. 1. This alternative resection 17 is formed by extending the calcar resection 12 from medial to lateral though the entire proximal femur 10.

More bone conserving cuts may also be formed in to the proximal femur 10 as shown in FIG. 1. These cuts may include a formed concentric region 15 that is larger in size but concentric to or aligned with the intramedullary cavity 25. These cuts may also include a transverse resection 13 that is cut relatively perpendicular to the intramedullary cavity 25.

To simplify the surgical procedure, the resections shown in FIG. 1 can all be formed by a single reamer (not shown). This reamer has a cutting surface formed in the shape of the combined profile of all of the resection cuts. It can be rotated or oscillated about the longitudinal axis 21 of the intramedullary canal 25, until the desire bone tissue is removed. As shown in FIG. 2, the various cuts that together form the proximal resection 20 pass through portions of both the relatively dense cortical bone 44 and the more porous cancellous bone 3. Thus, the cutting surfaces of the tissue removal tools are designed to cut both dense cortical bone 44 and less dense cancellous bone 3.

After the intramedullary cavity 25 and the proximal resection 20, including the calcar resection 12 and when applicable other bone tissue removal cuts are formed, the femoral stem component 100 can be inserted to mate with the exposed bone surfaces. The femoral stem component 100 comprises a proximal male friction fit portion 150, a distal neck body 160, a flange portion 200, a transitional body portion 300, an elongated stem portion 400, and a distal end tip portion 500. These portions will be discussed in detail below.

The femoral stem component 100 has a proximal male friction fit portion 150 on its most proximal end that is shaped to accept partially hemispherical femoral head component 700. One shape of the proximal male friction fit portion 150 is a cylindrical taper shape with the smaller diameter on the male friction fit portion proximal section 151, a tapered male friction fit portion 152 distal to the male friction fit portion proximal section 151, and a larger diameter male friction fit portion taper maximum cross-section bottom end 153 on the distal end of the male friction fit portion 152. The proximal male friction fit portion 150 could also be a straight cylindrical shape without a taper, or a series of successively larger diameter cylindrical shapes.

A femoral head component 700 has a male cavity 720 that is dimensioned to fit over and mate with the friction fit portion 152 of the proximal male friction fit portion 150 when the femoral head component 700 is assembled on the proximal male friction fit portion 150. The femoral head prosthesis 700 has an external bearing surface portion 710 on its external surface that is substantially on its proximal side when implanted. The external bearing surface portion 710 of the femoral head prosthesis 700 is substantially hemispherical shaped on a portion of its load bearing external bearing surface. This hemispherical shape is designed to mate with either an artificial prosthetic acetabular cup surface (not shown) as is the case for a total hip arthroplasty or a natural acetabular surface as is the case for a hip femoral hemiplasty.

The proximal male friction fit portion 150 has a male friction fit portion neck 154 that is distal to the male friction fit portion portion 152 and adjacent to the male friction fit portion taper bottom end 153. This male friction fit portion neck 154 functions as an undercut relief for the femoral head component 700 when assembled. Because the male friction fit portion neck 154 is smaller in diameter than the male friction fit portion portion 152, the femoral head component 700 can be pressed onto the proximal male friction fit portion 150 with the only direct contact between the two on the friction fit portion 152 of the femoral stem component 100 and the male friction fit portion 720 of the femoral head component 700.

The male friction fit portion neck 154 is proximal to and attached directly to a more bulky distal neck body 160. The distal neck body 160 is shaped to distribute the loads transmitted through the proximal male friction fit portion 150 from the femoral head component 700 through a flange portion 200 and a transitional body portion 300. The shape of the distal neck body 160 transitions from a simple symmetric shape similar to the cross-section of the male friction fit portion neck 154 to a more complex asymmetric shape that is similar to the combined shape of the flange portion 200 and the transitional body portion 300. In the embodiment shown in FIGS. 1 through FIG. 7, the cross-sectional shape of the distal neck body 160 at the proximal section is round because the male friction fit portion is a conical tapered and the male friction fit portion neck 154 is a cylindrical hourglass shape. However, the shape of the distal neck body 160 at the proximal section can be other shape to correspond with the shape of the proximal male friction fit portion 150.

The flange portion 200 has an upper portion 210 on its proximal side that contacts at least a part of the distal neck body 160. In the embodiments shown in FIGS. 1, 2, 3, 6 and 7 the flange portion is angled to match the at the same angle as the calcar resection 12 made by the surgeon on the proximal femur 10. The angle and the size of the flange portion 200 are dependent on the anatomy of the patient and the morphology of the calcar resection 12. The flange portion 200 has an anterior-posterior flange portion width 240 that is wide enough to cover at least a portion of the cortical bone tissue 44 that has been resected. The cortical bone tissue 44 is more rigid than the cancellous bone tissue 3. In a healthy hip joint, the compressive loads are transmitted through both the cancellous bone tissue and the cortical bone tissue 44 of the proximal femur 10. Because the cortical bone tissue 44 is more dense and rigid, and can sustain a higher load per square unit area without fracture than the cancellous bone tissue 3, cortical bone tissue 44 is a more efficient distributor of compressive loads than cancellous bone tissue 3. Thus, the flanged portion 200 is shaped to cover both the resected cancellous bone 3 and the resected cortical bone 44 so that the compressive loads transmitted through the flange portion 200 are distributed as anatomically close as possible to how they were distributed when the proximal femur 10 was healthy and intact.

Figure 4:
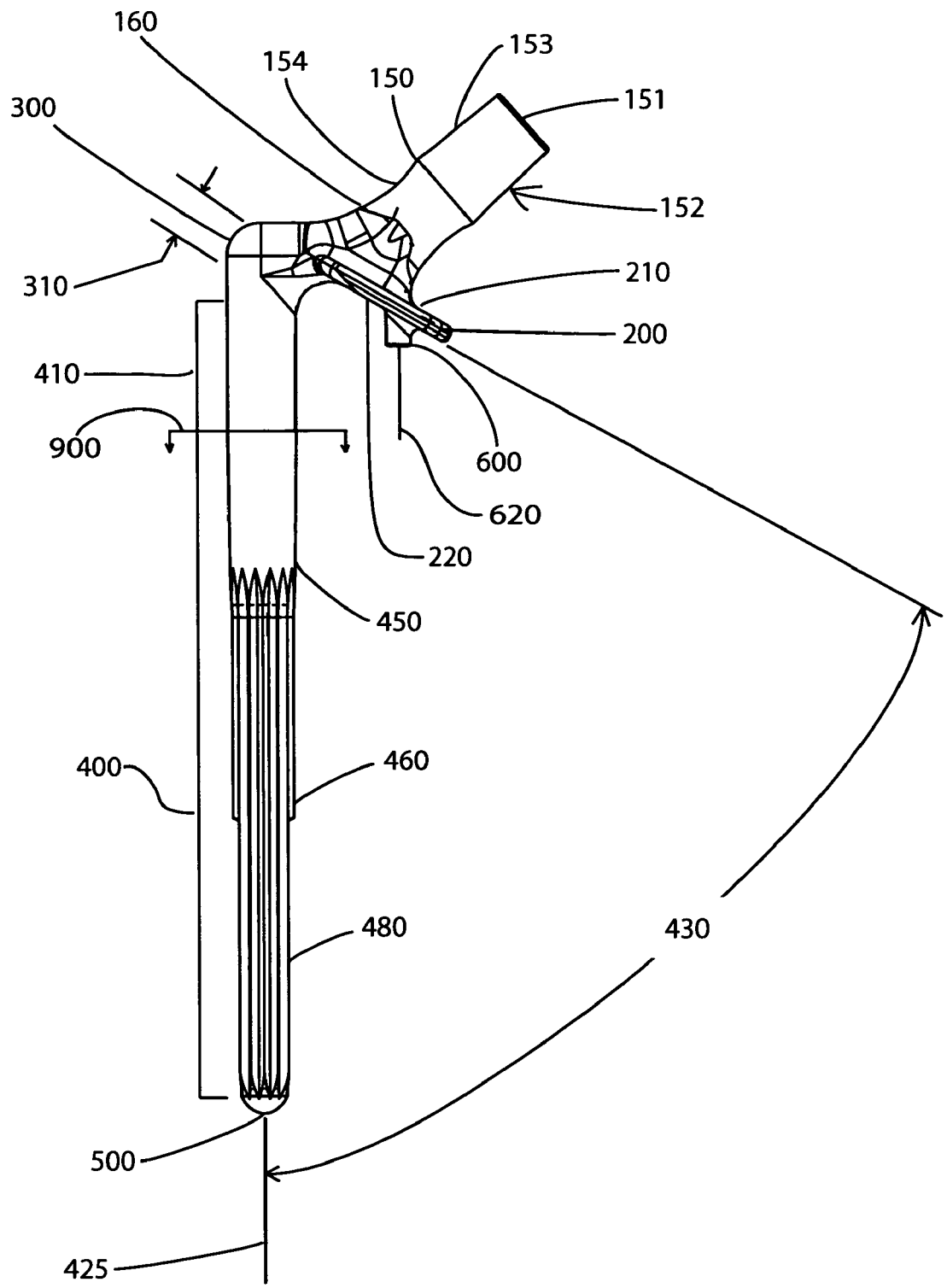
FIG. 4 is an anterior side view of the femoral hip prosthesis shown outside of the femur.
Figure 5:
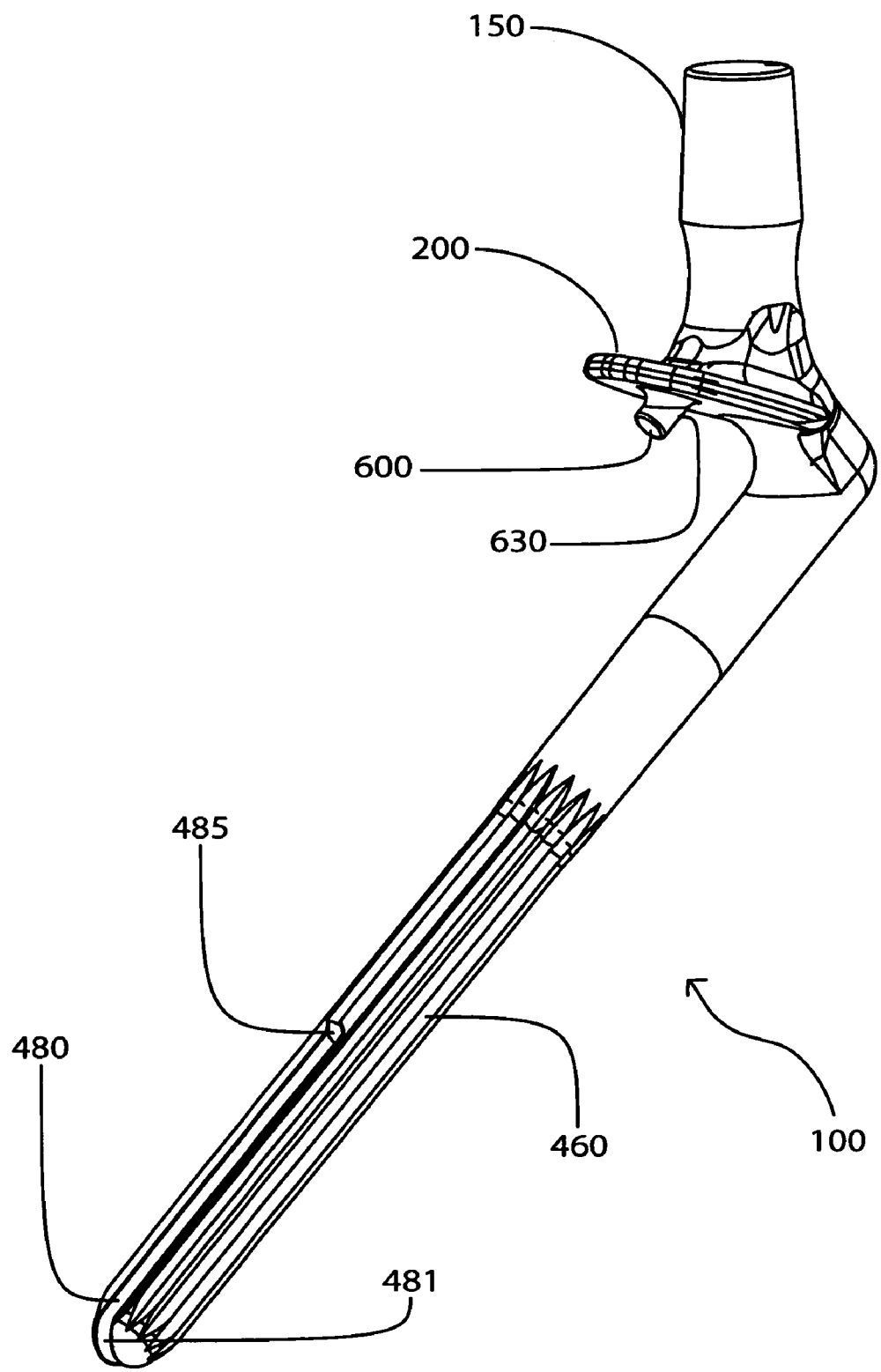
FIG. 5 is an isometric view of the medial side of the femoral stem component as it appears outside of the femur.

The flanged portion 200 is less thick than it is wide. As shown in the embodiment of FIG. 4, the flange portion thickness 221 is between 0.5 millimeters and 12 millimeters. The flange portion 200 is substantially thick enough to transmit loads from the hip joint to the calcar resection surface 12 of both the cancellous bone tissue 3 and the cortical bone tissue 44. The flange portion 200 is also thin enough to limit the about of bone that must be resected to form the calcar resection 12.

The transitional body region 300 is the portion of the femoral stem component 100 that transitions from the distal neck body 160 and the flange portion 200 to the distal elongated stem portion 400. The transitional body region 300 is adjacent to both the distal neck body 160 and the flange portion 200 on its proximal side and adjacent to the elongated stem portion 400 on its distal side. The transitional body portion 300 has a maximum height 310 that is the linear distance measured between a plane tangent to the bottom surface 220 of the flange portion 200 and a plane through the most distal part of the transitional body portion 300. In FIG. 4, these two planes are shown as lines since this is a side view. In the embodiment of the transitional body portion shown in FIG. 4, the transitional body portion 300 has a curved fillet 330 its medial side. Although this is shown as a round fillet in FIG. 4, the medial side of the transitional body portion 300 can be a chamfered fillet, a stepped fillet, or any other non-linear or linear shape that transitions from the shape of the elongated stem portion 400 to the shape of portions of the distal neck body 160 or the flange portion 200. The maximum height 310 of the majority of the transitional body region 300, when measured normal from the bottom surface 220 of the flange portion 200 to any part of the elongated stem portion 400 is less than thirteen millimeters or less. Both the physical structure of the femoral hip prosthesis 50, and the mechanical properties of the material from which the prosthesis is fabricated, function together to determine the functional strength and elasticity of the femoral stem component 100.

Conventional orthopedic alloys such as cobalt chrome, titanium and stainless steel alloys and orthopedic composite materials have proven to provide reasonable strength and rigidity to orthopedic implants and may also be used to fabricate the femoral stem component 100. However, when conventional orthopedic alloys or composites are fabricated into the eccentric conical shape of a typical femoral stem component 100, the resulting implant is more rigid than the proximal femoral 10 that the femoral stem component 100 is replacing. Flexibility of the stem component 100 is necessary to allow the flex and compliance desired to dynamically anatomically load the proximal femur 10 bone during biomechanical loading. The relatively small shape of the transitional body portion 300 allows for more flexion of the flange portion 200 when the proximal male friction fit portion 150 is loaded than is seen with the bulkier conventional eccentric cone shaped femoral prosthesis. The unique shape of the femoral stem component 100 allows for flexibility of the prosthesis even when fabricated from rigid orthopedic alloys such as such as cobalt chrome, titanium and stainless steel alloys.

This dynamic flexibility within the transitional portion 300 is desired since it allows the flange portion 200 of the femoral stem component 100 to transmit loads and displacements to the femoral calcar region 11 of the proximal femur 10. When bone is loaded and allowed to deform, a piezoelectric effect within the tissue simulate the bone cells into further production. This phenomenon, sometimes called Wolfs Law, coupled with other physiologic and biochemical principles, helps to keep the bone surrounding the femoral hip prosthesis 50 healthy and vibrant. The femoral stem component 100 is designed to optimize the effects that a flexible, yet strong femoral hip prosthesis 50 will have on the surrounding loaded bone tissue. As the hip joint is loaded during clinical use, loads are transmitted through the male friction fit portion 154 and distal neck body 160 to the flange portion 200 and the transitional body portion 300 to the stem. Since the transitional body portion 300 is relatively flexible and not as bulky and rigid as a conventional femoral hip prosthesis, the transitional body portion 300 allows the femoral stem component 100 to flex and transmit the compressive load to the bone in the calcar region 11 of the proximal femur 10. These loads on the bone may allow the dynamization necessary to keep the tissue surrounding the femoral stem component 100 healthy and help prevent bone resorption in the calcar region 11 of the proximal femur 10.

Distal and adjacent to the transitional body portion 300 is the elongated stem portion 400. The elongated stem portion 400 comprises some or all of the following portions and features; a tapered portion 450, a splined section 470, and transverse slot 480. The elongated stem portion is encompassed within a cylindrically shaped envelope referred to as uniform envelope 410. The cross-sectional shape and the area of the uniform envelope 410 remains substantially uniform throughout the longitudinal length of the elongated body. The uniform envelope 410 has a circular uniform cross-sectional periphery 902 that is defined by the maximum cross-sectional peripheral diameter 905 of the elongated stem portion 400. The uniform envelope 410 is the same length as the elongated stem portion. The elongated stem portion is adjacent to the transitional body portion 300 on its proximal end and adjacent to a distal tip portion 500 on its distal end.

As shown in FIG. 4, the elongated stem portion 400 is longitudinally aligned with a longitudinal axis 425. When the femoral stem component 100 is implanted in the proximal femur 10, the longitudinal axis 425 is approximately in alignment with the longitudinal axis 21 of the intramedullary cavity 25. All the possible features or portions of the elongated stem portion 400, including the tapered portion 450, the spine section 470, and the transverse slot 480 have cross-sections perpendicular to the longitudinal axis 425 and are contained within a maximum diameter 905 of a cross-sectional periphery 902 that defines the cross-section of the uniform envelope 410. Representative shapes of cross-sectional areas viewed from a cross-sectional view cut plane 900 are shown in FIG. 4a through FIG. 4e. Included in these figures are the cross-sectional periphery 902 and the maximum diameter 905 of the cross-sectional periphery 902.

Material may be removed from the elongated stem portion 400 to created features such as taper portions 450, splines 460 or the transverse slots 480. However, the basic substantial shape of the external periphery of the cross-section of the elongated stem portion 400 remains uniform and circular. Thus, the elongated stem portion and the uniform envelope 410 are both substantially symmetric and non-eccentric. The embodiment of the elongated stem portion 400 shown in FIG. 4 is substantially cylindrical in shape 910. The cross-section of this cylindrically shaped elongated stem portion is shown in FIG. 4a. However, for other embodiments of the femoral stem component 100, the cross-sectional shape of the elongated stem portion 400 can be also non-circular shapes such as substantially square shape 920, as shown in FIG. 4b; a substantially triangle shape 930, as shown in FIG. 4c; a substantially hexagonal shape 940, as shown in FIG. 4c, a substantially star shape 950 as shown in FIG. 4e, or any other substantially non-eccentric, symmetric shape such as a tube (not shown) that can functionally form the cross-section of the elongated stem portion 400.

In the embodiments shown, the longitudinal axis 425 of the elongated stem portion 400 is a substantially straight axis throughout the length of the elongated stem portion 400. However, to better match the anatomy of the proximal femur 10, the longitudinal axis 425 can also be curved. The curve may be in the anterior-posterior plane, the medial-lateral plane or a compound curve that is seen in both the anterior-posterior plane and the medial-lateral plane. A flexible reamer (not shown) could be used to form the curved intramedullary cavity before the prosthesis 10 with a curved longitudinal axis 425 is implanted.

The elongated stem portion 400 may include a tapered portion 450 along its length. This is shown in FIG. 2. This tapered portion 450 may also include splines 460 or transverse slots 480 cut into it. The cross-sectional area of the tapered portion 450 in the embodiments shown decreases linearly along the longitudinal length of the tapered portion 450 as the tapered portion 450 transitions down the length of the elongated stem portion 400 from proximal to distal. The direction of the tapered portion 450 may also be in the opposite direction. The tapered area in the elongated portion 400 allows for greater flexibility in bending along the tapered portion 450 due to the reduced cross-sectional area and reduced cross-sectional bending moment of inertia. The tapered portion 450 also allows for an interference tapered wedge fit between the elongated stem portion 400 and the intramedullary cavity 25 in the proximal femur 10 when the cross-sectional size of the intramedullary canal 25 is less than the maximum diameter 905 of the periphery 902.

Features such the splines 460 are cut into the elongated stem portion 400 for various structural and functional reasons such as to provide additional torsional resistance to the femoral stem component 100. In the embodiments shown, the splines 460 are evenly spaced around the periphery 902 of the distal elongated stem portion 400. The splines 460 are cut longitudinal around the periphery 902 of the elongated stem portion 400. This allows the splines 460 to resist axial rotation between the femoral stem component 100 and the intramedullary cavity 25. The splines 460 may also provide additional structural flexibility to the distal end of the femoral stem component 100.

At the distal end of the femoral stem component 100, an optional longitudinal transverse slot 480 may be cut transversely into the elongated stem portion 400 to provide additional flexibility and potentially additional torsional resistance to the femoral stem component 100. The embodiment of the slot 480 that is shown is substantially uniform in cross-sectional and in shape though its length. The cross-sectional shape of the slot 480 may also be non-uniform. The cross-sections shape of the slot 480 may also change. For example the sides of the slot 481 may change from parallel planar surfaces to non-parallel or non-planar surfaces as the slot transitions from distal to proximal. The slot 480 also has a fillet 485 that takes the form of a rounded radius shape at its most proximal end. The shape of this fillet 485 may be other shapes that allow a relatively smooth transition from the slot 480 to the non-slotted cross-section. For example the slot 480 may be keyhole shaped.

Adjacent and distal to the elongated stem portion is the distal end tip portion 500. The distal end tip portion 500 has a lead-in section 510 that reduces in cross-sectional area from proximal to distal. The lead-in section may be tapered as in the embodiment of FIG. 3, or spherical as in the embodiment of FIG. 4, or any shape that is successively smaller in cross-sectional area from proximal to distal. The distal end tip portion 500 helps to guide the femoral stem component 100 into the intramedullary canal 25. The relatively smooth shape of the distal end tip portion 500 also functions to reduce the stress on the proximal femoral bone associated with discontinuity of terminating a rigid prosthesis in the intramedullary canal 25.

Figure 6:
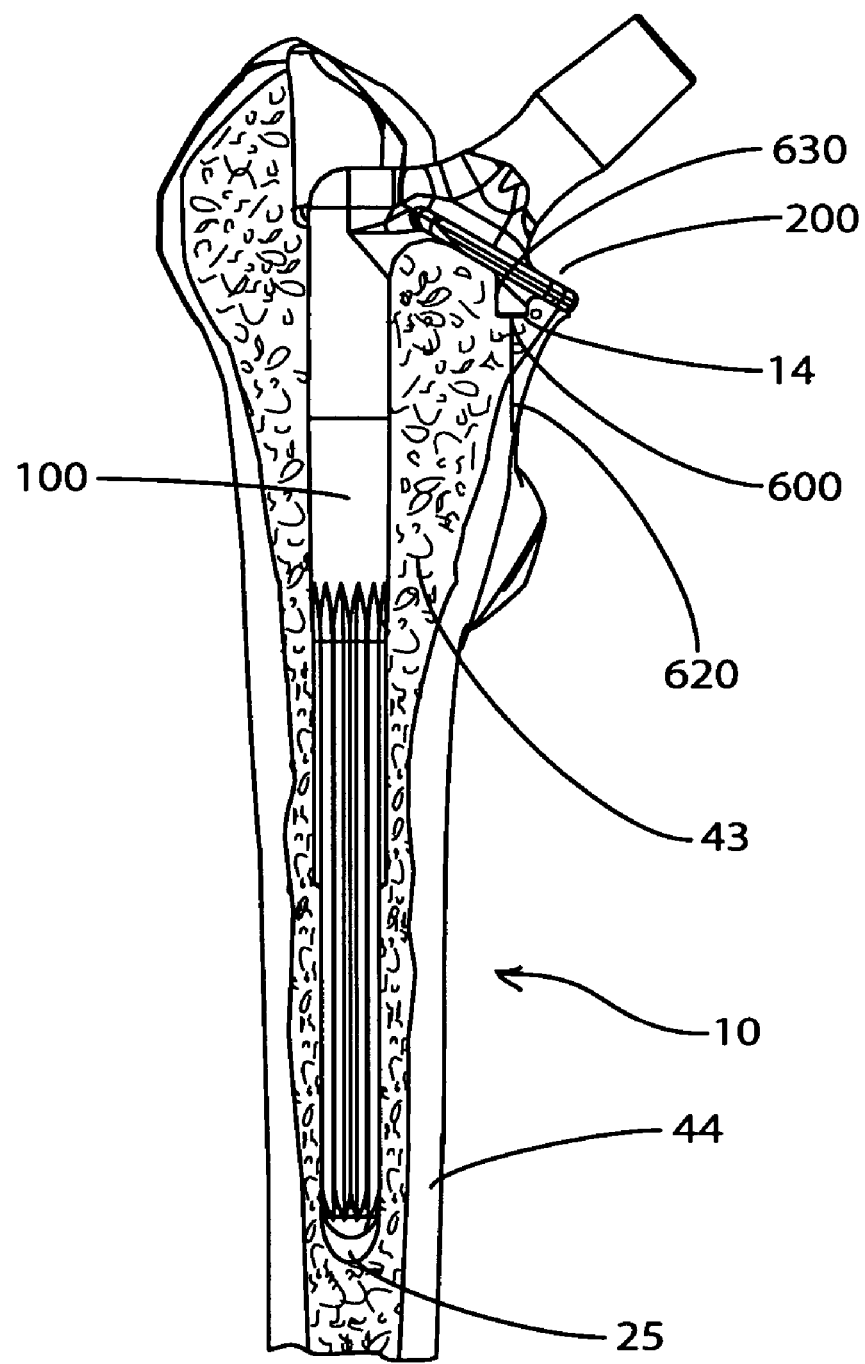
FIG. 6 is a cross-sectional view of the proximal femur from the anterior side showing the positioning of the femoral stem component inside of the proximal femur.

The load distribution on the proximal femur 10 of an intact hip joint can be essentially resolved into an axial component, a bending moment in the medial and lateral direction, a bending moment in the anterior posterior direction, and a torsional moment with a rotational axis approximately in line with the longitudinal axis 21 of the proximal femur. The distribution of the magnitude and direction of these force components depend upon complex combinations of biomechanical factors such as leg stance, patient weight distribution, and patient gait. The femoral stem component 100 is designed to translate these forces to anatomic loads on the proximal femur 10. As described above, the flange portion 200 helps to translate the compressive loads to the cancellous bone 3 and cortical bone 4 in the calcar region 11. The elongated stem portion 400 helps to transmit the bending and torsional moments to the intramedullary canal 25. In addition, a rotation-restricting boss 600 helps to transmit some of the torsional moments to the bone in the calcar region 11 of the proximal femur 10. As shown in FIG. 6, the boss periphery 630 of the rotation-restricting boss 600 interfaces with the bone surrounding the boss cavity 14. This structural interference between the femoral stem component 100 and the proximal femur 10 helps to restrict rotation, caused by the above-described resultant torsional moment with approximately in line with the longitudinal axis 21 of the proximal femur 10, between the femoral stem component 100 and the intramedullary cavity 25.

The size and location of the rotation-restricting boss 600 are factors that affect the amount that the rotation-restricting boss 600 restricts rotational movement of the femoral stem component 100. Due to greater resistance from a rotation-restricting boss with a larger resultant moment arm, the further that the rotation-restricting boss 600 is located from the longitudinal axis 425 of the elongated stem portion 400, the more effective it is in transmitting rotational loads and restricting rotational movement of the femoral stem component 100 to the proximal femur 10. Also, the larger the cross-sectional area of the rotation-restricting boss 600, the more effective it is in distributing torsion and restricting rotational movement of the femoral stem component 100.

The embodiments of the rotation-restricting boss 600 that are shown by example are circular in cross-section resulting in a cylindrical shaped boss. However, other cross-sectional shapes such as square, rectangular, triangular or diamond shapes may be more practical to machine or may be better at distributing torsional loads from the femoral hip prosthesis 50 to the proximal femur 10 than the shown cylindrically shaped rotation-restricting boss 600. The optimized shape of the rotation-restricting boss 600 may be more fin shaped than cylindrical shaped or longer than it is wide. This shape is partially dependent on the mechanical characteristics of the bone tissue where the rotation-restricing boss 600 is inserted.

The rotation restricting boss 600 has an axis of protrusion 620 with origin 621 substantially on a plane tangent or coincident with the bottom surface 220 of the flange portion 200. The boss axis of protrusion origin 621 and the stem portion longitudinal axis 425 are spaced apart by a length this is more than the maximum length 905 of the cross-section of the periphery 902 of the uniform envelope 410 of the elongated stem portion 400.

Figure 3:
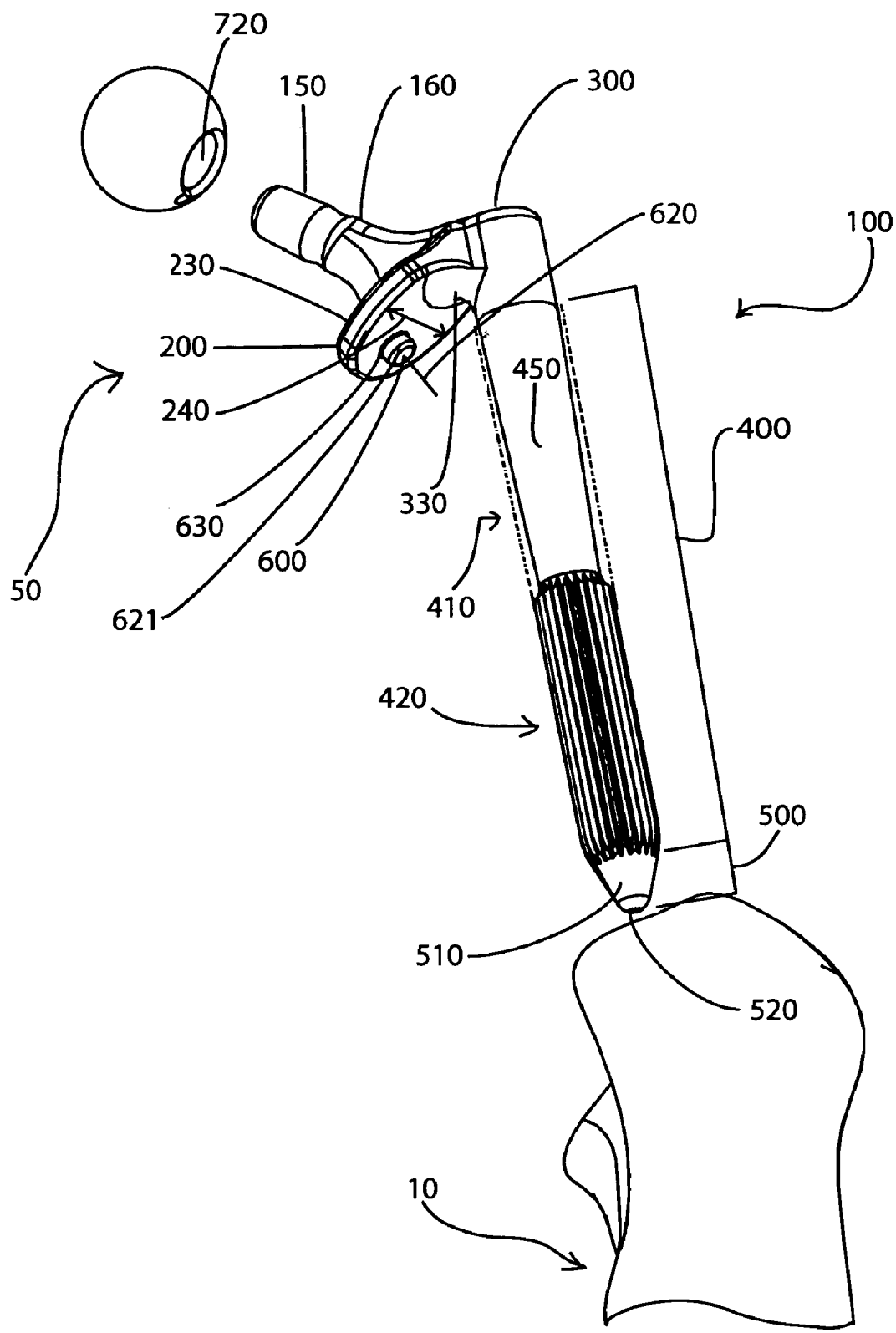
FIG. 3 is a perspective view shown from the posteriorolateral position showing the before it is inserted into the resected proximal femur.

The rotation-restricting boss 600 in the embodiment of the prosthesis 10 shown in FIG. 3 has an axis of protrusion that is substantially normal to the bottom surface 220 of the flange portion 200. The rotation-restricting boss in the embodiment of the prosthesis 10 shown in FIG. 4, FIG. 5 and FIG. 6 has an axis of protrusion 620 that is substantially parallel with the longitudinal axis 425 of the elongated stem portion 400. As shown in cross-section of the proximal femur illustrated in FIG. 6, the corresponding boss cavity 14 is in line with the axis of protrusion 620.

Figure 7:
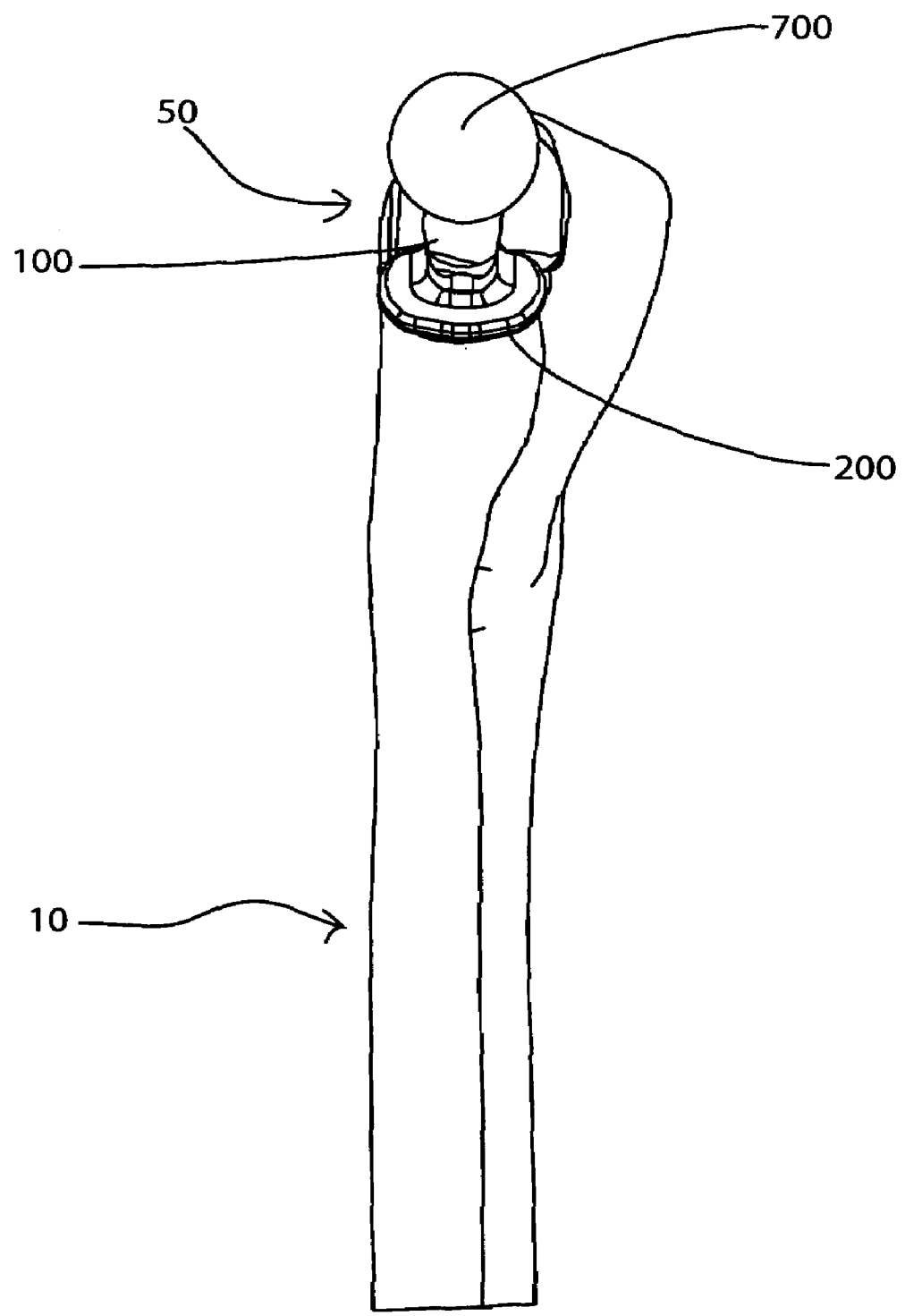
FIG. 7 is a medial view of the femoral hip prosthesis inside of the proximal femur.

As shown in FIG. 6 and FIG. 7, after the femoral stem component 100 is implanted in the proximal femur 10, the flange portion 200 is pressed against a resected surface 20 on the proximal femur 10, and the elongated stem portion 400 is pressed in the intramedullary cavity 25 aligned with the long axis of the proximal femur 10. As the femoral head 700 is loaded by the hip joint, a substantial component of the axial compressive force is transmitted to the cancellous 3 and cortical 4 bone in the calar region 11 from the flange portion 200. The principle torsional loads are transmitted to the splines 460, slot 480 and rotational-restricting boss 600 and the principle bending loads are transmitted to the intramedullary canal 25 through the elongated stem portion 400. Collectively, these feature and portions of the femoral hip prosthesis 10 contribute to distribute anatomical loads from hip joint to the remaining proximal femoral bone tissue.

While the present invention has been disclosed in its preferred form, the specific embodiments thereof as disclosed and illustrated herein are not to be considered in a limiting sense, as numerous variations are possible. The invention may be embodied in other specific forms without departing from its spirit or essential characteristics. The described embodiments are to be considered in all respects only as illustrative and not restrictive. No single feature, function, element or property of the disclosed embodiments is essential. The scope of the invention is, therefore, indicated by the appended claims rather than by the foregoing description. The following claims define certain combinations and sub-combinations that are regarded as novel and non-obvious. Other combinations and subcombinations of features, functions, elements and/or properties may be claimed through amendment of the present claims or presentation of new claims in this or related applications. Such claims, whether they are broader, narrower or equal in scope to the original claims, are also regarded as included within the subject matter of applicant's invention. All changes that come within the meaning and range of equivalency of the claims are to be embraced within their scope.

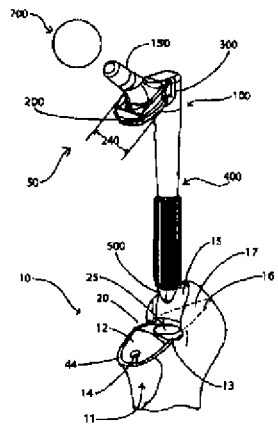

What is claimed is:

1. A prosthesis adapted for implantation against a resected surface on a proximal end of a femur and inside of an intramedullary cavity of the femur, the prosthesis comprising:
    a femoral head component comprising an external bearing surface; and
    a femoral stem component comprising:
        a neck portion comprising a proximal portion, engagable with the femoral head component, and a distal neck body;
        a flange portion distal and adjacent to the neck portion, the flange portion comprising a bottom surface;
        a transitional body region adjacent to the bottom surface of the flange portion and extending from the distal neck body; and
        an elongated stem portion extending distally from the transitional body region and having a longitudinal axis oriented at an acute angle from the bottom surface of the flange portion;
        wherein the transitional body region is shaped to flex such that, during a normal gait cycle, the bottom surface exerts a significant compressive load on the resected surface of the femur.

2. A prosthesis as is claim 1, wherein the elongated stem portion comprises a uniform envelope with a substantially constant cross-sectional peripheral shape and size.

3. A prosthesis as in claim 1, wherein the elongated stem portion comprises a proximal section having a cross sectional shape that is substantially consistent along a longitudinal length of the proximal section, wherein a minimum displacement between the bottom surface of the flange and the proximal section, measured normal to the bottom surface, is less than thirteen millimeters.

4. A prosthesis as in claim 1, further comprising a rotation-restricting boss, extending from the bottom of the flange portion.

5. A prosthesis as in claim 2, further comprising a rotation-restricting boss, extending from the bottom of the flange portion.

6. A prosthesis as in claim 5, wherein the rotation restricting boss has an axis of protrusion with a boss axis origin near the bottom surface of the flange, the elongated stem also has a stem axis origin near the bottom of the flange, the boss axis origin and the stem axis origin are spaced apart by a length more than the maximum cross-section of the elongated stem portion.

7. A prosthesis as in claim 6, wherein the axis of protrusion and the longitudinal axis are substantially parallel.

8. A prosthesis as in claim 6, wherein the axis of protrusion and the longitudinal axis are not substantially parallel.

9. A prosthesis as in claim 6, wherein the axis of protrusion is normal to the bottom surface of the flange portion.

10. A prosthesis as in claim 1, wherein the elongated stem portion has a distal section with multiple longitudinal flutes, wherein the longitudinal flutes are aligned approximately parallel to the longitudinal axis.

11. A prosthesis as in claim 1, wherein the neck portion is aligned at an obtuse angle with respect to the bottom surface of the flange portion.

12. A prosthesis as in claim 11, wherein the obtuse angle is between 100° and 170°.

13. A prosthesis as in claim 1, wherein the neck portion has a first end and a second end, wherein the first end is connected to the flange portion and extends proximally therefrom and the second end is shaped to press-fit into the femoral head component.

14. A prosthesis as in claim 13, wherein at least a portion of the outer surface of the femoral head component is hemi-spherical.

15. A prosthesis as in clam 1, wherein the acute angle ranges from 15° to 80°.

16. A prosthesis as in claim 2, wherein the uniform envelope has a maximum cross-section area measured on a plane perpendicular to the longitudinal axis.

17. A prosthesis as in claim 1, wherein the elongated stem portion has a length of at least one hundred millimeters as measured along the length of its longitudinal axis.

18. A prosthesis as in claim 1, wherein the elongated stem portion comprises a tapered portion.

19. A prosthesis as in claim 1, wherein the elongated stem portion comprises a proximal section having a cross sectional shape that is substantially consistent along a longitudinal length of the proximal section, wherein a minimum displacement between the bottom surface of the flange and the proximal section, measured normal to the bottom surface, is less than a maximum cross sectional width of the elongated stem portion, measured perpendicular to the longitudinal axis.

20. A prosthesis as in claim 1, wherein the transitional body region is shaped to provide a lateral offset between an axis of the neck portion and the longitudinal axis of the elongated stem portion.

* * * * *

UNITED STATES PATENT AND TRADEMARK OFFICE
CERTIFICATE OF CORRECTION

PATENT NO.        : 7,534,271 B2
APPLICATION NO.   : 10/763314
DATED             : May 19, 2009
INVENTOR(S)       : Michael Ries et al.

It is certified that error appears in the above-identified patent and that said Letters Patent is hereby corrected as shown below:

Column 12, line 54, insert the following 16 claims:
--21. A prosthesis adapted for implantation against a resected surface on a proximal end of a femur and inside of a cavity of the femur, comprising:
a femoral head component comprising an external bearing surface; and
a femoral stem component comprising:
a neck portion shaped to extend substantially outside the cavity of the femur, the neck portion having a proximal portion, engagable with the femoral head component, and a distal neck body;
a flange portion medially and distally projecting from the neck body, the flange portion comprising a bottom surface;
an elongated stem portion shaped to extend substantially inside the cavity of the femur and extending distally from the neck body and having a longitudinal axis oriented at an acute angle from the bottom surface of the flange portion;
wherein, distally of a medial tip of the flange, each cross sectional shape along substantially an entire length of the elongated stem portion is substantially radially symmetrical.
22. A prosthesis as in claim 21, wherein, distally of a medial juncture of the neck portion with the flange, each cross sectional shape along substantially the entire length of the elongated stem portion is substantially radially symmetrical.
23. A prosthesis as in claim 21, wherein each cross sectional shape is selected from the group consisting of a circle, a rectangle, a triangle, a hexagon, and a star shape.
24. A prosthesis as in claim 21, wherein the elongated stem portion comprises a proximal section having a substantially circular shape, and a distal section having a non-circular cross sectional shape.
25. A prosthesis as in claim 21, wherein, distally of a medial tip of the flange, substantially an entire length of the elongated stem portion is circumscribed by a substantially cylindrical shape.
26. A prosthesis as in claim 25, wherein, distally of a medial tip of the flange, any two maximum cross sectional widths of the elongated stem portion, measured perpendicular to the longitudinal axis, do not differ by more than ten percent.

Signed and Sealed this
Twenty-eighth Day of August, 2012

David J. Kappos
*Director of the United States Patent and Trademark Office*

27. A prosthesis as in claim 21, wherein the femoral stem component further comprises a transitional body region adjacent to the bottom surface of the flange portion, wherein the transitional body region is shaped to provide a lateral offset between an axis of the neck portion and the longitudinal axis of the elongated stem portion.

28. A prosthesis adapted for implantation against a resected surface on a proximal end of a femur and inside of a cavity of the femur, comprising:

a femoral head component comprising an external bearing surface; and a femoral stem component comprising:

a neck portion shaped to extend substantially outside the cavity of the femur, the neck portion having a proximal portion, engagable with the femoral head component, and a distal neck body;

a flange portion medially and distally projecting from the neck body, the flange portion comprising a bottom surface;

an elongated stem portion shaped to extend substantially inside the cavity of the femur and extending distally from the neck body and having a longitudinal axis oriented at an acute angle from the bottom surface of the flange portion;

wherein, distally of a medial tip of the flange, substantially an entire length of the elongated stem portion is circumscribed by a substantially cylindrical shape.

29. A prosthesis as in claim 28, wherein, distally of a medial juncture of the neck portion with the flange, substantially the entire length of the elongated stem portion is circumscribed by the substantially cylindrical shape.

30. A prosthesis as in claim 28, wherein the elongated stem portion comprises a proximal section having a substantially circular shape, and a distal section having a non-circular cross sectional shape.

31. A prosthesis as in claim 28, wherein, distally of a medial tip of the flange, any two maximum cross sectional widths of the elongated stem portion, measured perpendicular to the longitudinal axis, do not differ by more than ten percent.

32. A prosthesis as in claim 28, wherein the femoral stem component further comprises a transitional body region adjacent to the bottom surface of the flange portion, wherein the transitional body region is shaped to provide a lateral offset between an axis of the neck portion and the longitudinal axis of the elongated stem portion.

33. A prosthesis adapted for implantation against a resected surface on a proximal end of a femur and inside of a cavity of the femur, comprising:

a femoral head component comprising an external bearing surface; and a femoral stem component comprising:

a neck portion shaped to extend substantially outside the cavity of the femur, the neck portion having a proximal portion, engagable with the femoral head component, and a distal neck body;

a flange portion medially and distally projecting from the neck body, the flange portion comprising a bottom surface;

an elongated stem portion shaped to extend substantially inside the cavity of the femur and extending distally from the neck body and having a longitudinal axis oriented at an acute angle from the bottom surface of the flange portion;

wherein, distally of a medial tip of the flange, any two maximum cross sectional widths of the elongated stem portion, measured perpendicular to the longitudinal axis, do not differ by more than ten percent.

34. A prosthesis as in claim 33, wherein, distally of a medial juncture of the neck portion with the flange, any two maximum cross sectional widths of the elongated stem portion, measured perpendicular to the longitudinal axis, do not differ by more than ten percent.
35. A prosthesis as in claim 33, wherein the elongated stem portion comprises a proximal section having a substantially circular shape, and a distal section having a non-circular cross sectional shape.
36. A prosthesis as in claim 33, wherein the femoral stem component further comprises a transitional body region adjacent to the bottom surface of the flange portion, wherein the transitional body region is shaped to provide a lateral offset between an axis of the neck portion and the longitudinal axis of the elongated stem portion.--

UNITED STATES PATENT AND TRADEMARK OFFICE
CERTIFICATE OF CORRECTION

PATENT NO. : 7,534,271 B2  
APPLICATION NO. : 10/763314  
DATED : May 19, 2009  
INVENTOR(S) : Michael Ries et al.

Page 1 of 4

It is certified that error appears in the above-identified patent and that said Letters Patent is hereby corrected as shown below:

Delete the title page and substitute therefore the attached title page showing the corrected number of claims in patent.

Column 12, line 54, insert the following 16 claims:
--21. A prosthesis adapted for implantation against a resected surface on a proximal end of a femur and inside of a cavity of the femur, comprising:
a femoral head component comprising an external bearing surface; and
a femoral stem component comprising:
a neck portion shaped to extend substantially outside the cavity of the femur, the neck portion having a proximal portion, engagable with the femoral head component, and a distal neck body;
a flange portion medially and distally projecting from the neck body, the flange portion comprising a bottom surface;
an elongated stem portion shaped to extend substantially inside the cavity of the femur and extending distally from the neck body and having a longitudinal axis oriented at an acute angle from the bottom surface of the flange portion;
wherein, distally of a medial tip of the flange, each cross sectional shape along substantially an entire length of the elongated stem portion is substantially radially symmetrical.
22. A prosthesis as in claim 21, wherein, distally of a medial juncture of the neck portion with the flange, each cross sectional shape along substantially the entire length of the elongated stem portion is substantially radially symmetrical.
23. A prosthesis as in claim 21, wherein each cross sectional shape is selected from the group consisting of a circle, a rectangle, a triangle, a hexagon, and a star shape.
24. A prosthesis as in claim 21, wherein the elongated stem portion comprises a proximal section having a substantially circular shape, and a distal section having a non-circular cross sectional shape.

This certificate supersedes the Certificate of Correction issued August 28, 2012.

Signed and Sealed this  
Eighteenth Day of September, 2012

David J. Kappos  
*Director of the United States Patent and Trademark Office*

25. A prosthesis as in claim 21, wherein, distally of a medial tip of the flange, substantially an entire length of the elongated stem portion is circumscribed by a substantially cylindrical shape.

26. A prosthesis as in claim 25, wherein, distally of a medial tip of the flange, any two maximum cross sectional widths of the elongated stem portion, measured perpendicular to the longitudinal axis, do not differ by more than ten percent.

27. A prosthesis as in claim 21, wherein the femoral stem component further comprises a transitional body region adjacent to the bottom surface of the flange portion, wherein the transitional body region is shaped to provide a lateral offset between an axis of the neck portion and the longitudinal axis of the elongated stem portion.

28. A prosthesis adapted for implantation against a resected surface on a proximal end of a femur and inside of a cavity of the femur, comprising:
a femoral head component comprising an external bearing surface; and
a femoral stem component comprising:
a neck portion shaped to extend substantially outside the cavity of the femur, the neck portion having a proximal portion, engagable with the femoral head component, and a distal neck body;
a flange portion medially and distally projecting from the neck body, the flange portion comprising a bottom surface;
an elongated stem portion shaped to extend substantially inside the cavity of the femur and extending distally from the neck body and having a longitudinal axis oriented at an acute angle from the bottom surface of the flange portion;
wherein, distally of a medial tip of the flange, substantially an entire length of the elongated stem portion is circumscribed by a substantially cylindrical shape.

29. A prosthesis as in claim 28, wherein, distally of a medial juncture of the neck portion with the flange, substantially the entire length of the elongated stem portion is circumscribed by the substantially cylindrical shape.

30. A prosthesis as in claim 28, wherein the elongated stem portion comprises a proximal section having a substantially circular shape, and a distal section having a non-circular cross sectional shape.

31. A prosthesis as in claim 28, wherein, distally of a medial tip of the flange, any two maximum cross sectional widths of the elongated stem portion, measured perpendicular to the longitudinal axis, do not differ by more than ten percent.

32. A prosthesis as in claim 28, wherein the femoral stem component further comprises a transitional body region adjacent to the bottom surface of the flange portion, wherein the transitional body region is shaped to provide a lateral offset between an axis of the neck portion and the longitudinal axis of the elongated stem portion.

33. A prosthesis adapted for implantation against a resected surface on a proximal end of a femur and inside of a cavity of the femur, comprising:
a femoral head component comprising an external bearing surface; and
a femoral stem component comprising:
a neck portion shaped to extend substantially outside the cavity of the femur, the neck portion having a proximal portion, engagable with the femoral head component, and a distal neck body;
a flange portion medially and distally projecting from the neck body, the flange portion comprising a bottom surface;
an elongated stem portion shaped to extend substantially inside the cavity of the femur and extending distally from the neck body and having a longitudinal axis oriented at an acute angle from the bottom surface of the flange portion;

wherein, distally of a medial tip of the flange, any two maximum cross sectional widths of the elongated stem portion, measured perpendicular to the longitudinal axis, do not differ by more than ten percent.

34. A prosthesis as in claim 33, wherein, distally of a medial juncture of the neck portion with the flange, any two maximum cross sectional widths of the elongated stem portion, measured perpendicular to the longitudinal axis, do not differ by more than ten percent.

35. A prosthesis as in claim 33, wherein the elongated stem portion comprises a proximal section having a substantially circular shape, and a distal section having a non-circular cross sectional shape.

36. A prosthesis as in claim 33, wherein the femoral stem component further comprises a transitional body region adjacent to the bottom surface of the flange portion, wherein the transitional body region is shaped to provide a lateral offset between an axis of the neck portion and the longitudinal axis of the elongated stem portion.--

(12) United States Patent
Ries et al.

(10) Patent No.: US 7,534,271 B2
(45) Date of Patent: May 19, 2009

(54) FEMORAL HIP PROSTHESIS AND METHOD OF IMPLANTATION

(75) Inventors: Michael Ries, Tiburon, CA (US); T. Wade Fallin, Hyde Park, UT (US); Daniel F. Justin, Logan, UT (US); Mark A. Munt, Moab, UT (US)

(73) Assignee: Smith + Nephew, Memphis, TN (US)

( * ) Notice: Subject to any disclaimer, the term of this patent is extended or adjusted under 35 U.S.C. 154(b) by 562 days.

(21) Appl. No.: 10/763,314

(22) Filed: Jan. 22, 2004

(65) Prior Publication Data
US 2005/0165493 A1  Jul. 28, 2005

(51) Int. Cl.
*A61F 2/36* (2006.01)

(52) U.S. Cl. .................... 623/23.21; 623/23.35

(58) Field of Classification Search .......... 623/23.21, 623/23.22, 23.24, 23.25, 23.26, 23.35
See application file for complete search history.

(56) References Cited

U.S. PATENT DOCUMENTS

| | | |
|---|---|---|
| 3,512,184 A | 5/1970 | Grove |
| 3,658,056 A | 4/1972 | Huggler et al. |
| 3,683,421 A | 8/1972 | Martinie |
| 3,782,373 A | 1/1974 | Smythe |
| 3,848,272 A | 11/1974 | Noiles |
| 3,864,758 A | 2/1975 | Yakich |
| 3,871,031 A | 3/1975 | Boutin |
| 3,894,297 A | 7/1975 | Mittelmeier et al. |
| 3,916,451 A | 11/1975 | Buechel et al. |
| 4,001,897 A | 1/1977 | Rambert et al. |
| 4,005,495 A | 2/1977 | Locke et al. |
| 4,012,795 A | 3/1977 | Dorre et al. |
| 4,012,796 A | 3/1977 | Weisman et al. |
| 4,021,865 A | 5/1977 | Charnley |
| 4,080,666 A | 3/1978 | Fixel |
| 4,129,903 A | 12/1978 | Huggler |
| 4,187,559 A | 2/1980 | Grell et al. |
| 4,224,699 A | 9/1980 | Weber |
| 4,274,164 A | 6/1981 | Rehder et al. |
| 4,312,079 A | 1/1982 | Dorre et al. |
| 4,314,381 A | 2/1982 | Koeneman |
| 4,332,036 A | 6/1982 | Sutter et al. |
| 4,454,612 A | 6/1984 | McDaniel et al. |
| 4,488,320 A | 12/1984 | Wilson |

(Continued)

FOREIGN PATENT DOCUMENTS

EP   159510 A2   3/1985

(Continued)

*Primary Examiner*—Bruce E Snow
(74) *Attorney, Agent, or Firm*—David W. Meibos; Daniel F. Justin; Barbara Daniels

(57) ABSTRACT

Implants and methods are presented for surgically repairing a hip joint with a proximal femoral prosthesis that comprises femoral head component and a femoral stem component. The femoral stem component comprising a neck portion, a flange portion, a transitional body region and an elongated stem. The femur is prepared for implantation of the femoral hip prosthesis by resecting the proximal femur and reaming a symmetric intramedullary cavity in the femur. The femoral hip prosthesis is then inserted the on the resected femur and in the intramedullary cavity. The femoral hip prosthesis elastically deforms when loaded during use to apply dynamic compressive loads and displacement to the calcar region of the resected proximal femur.

36 Claims, 8 Drawing Sheets